United States Patent [19]

Manabe et al.

[11] Patent Number: 5,055,589

[45] Date of Patent: Oct. 8, 1991

[54] INDOLENINE DERIVATIVE

[75] Inventors: Osamu Manabe; Shigeo Fujita; Shizuo Iwata; Morihiro Kamiyama, all of Osaka, Japan

[73] Assignee: Asahi Chemical Co., Ltd., Osaka, Japan

[21] Appl. No.: 490,591

[22] PCT Filed: Sep. 14, 1989

[86] PCT No.: PCT/JP89/00944

§ 371 Date: May 14, 1990

§ 102(e) Date: May 14, 1990

[87] PCT Pub. No.: WO90/02735

PCT Pub. Date: Mar. 22, 1990

[30] Foreign Application Priority Data

Sep. 16, 1988 [JP] Japan ................. 63-233275

[51] Int. Cl.$^5$ ................. A61K 31/40; C07D 209/56; C07D 209/04; C07D 491/00
[52] U.S. Cl. .................. 548/427; 548/490; 548/430
[58] Field of Search .......... 548/490, 430, 427; 514/411

[56] References Cited

U.S. PATENT DOCUMENTS 4,062,870 12/1977 Watts ................. 548/430

Primary Examiner—Mary C. Lee
Assistant Examiner—Robert C. Whittenbaugh
Attorney, Agent, or Firm—Armstrong, Nikaido, Marmelstein, Kubovcik & Murray

[57] ABSTRACT

The present invention provides an indolenine derivative represented by the formula

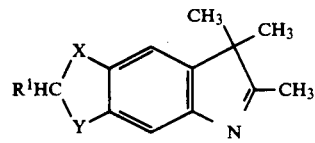

wherein $R^1$ is a hydrogen atom or a lower alkyl group, X and Y are the same or different and each represent a methylene group or an oxygen atom. This indolenine derivative is useful as an intermediate for synthesizing a cyanine compound suitable for use as an organic near infrared light-absorbing dye useful as an optical disc recording medium adapted for semiconductor laser recording.

5 Claims, No Drawings

INDOLENINE DERIVATIVE

FIELD OF THE INVENTION

The present invention relates to novel indolenine derivatives.

DISCLOSURE OF THE INVENTION

The indolenine derivative of the present invention is a compound undisclosed in literature and is represented by the formula (1)

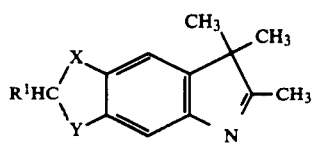

wherein $R^1$ is a hydrogen atom or a lower alkyl group, X and Y are the same or different and each represent a methylene group or an oxygen atom.

The compounds of the present invention represented by the formula (1) are useful as an intermediate for synthesizing the cyanine compounds represented by the formula (8) which appear hereinafter.

The compounds of the present invention can be prepared by various processes, and can be easily prepared, for example, by the following preferable process.

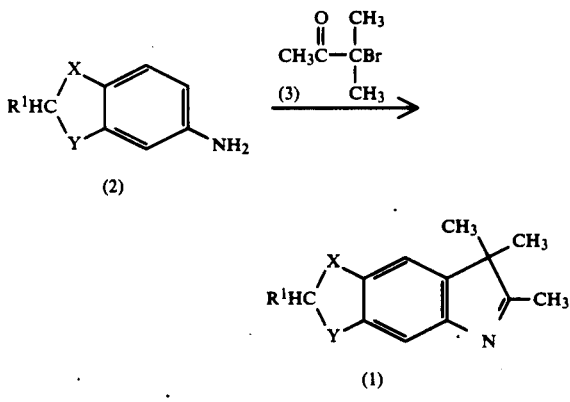

The conventional aniline derivative of the formula (2) is reacted with the conventional 3-bromo-3-methyl-2-butanone of the formula (3) in the presence of an acid scavenger. Useful acid scavengers are, for example, pyridine, triethylamine, tri-n-propylamine, tri-n-butylamine and like tertiary amines; sodium carbonate, potassium carbonate, calcium carbonate and like alkali metal salts of carbonic acids; sodium acetate, potassium acetate, calcium acetate and like alkali metal salts of acetic acids; etc. The acid scavenger is used in an amount of usually about 0.3 to about 5 moles, preferably about 0.5 to about 1.5 moles, per mole of the compound of the formula (2). The proportions of the compounds of the formulas (2) and (3) are usually about 0.3 to about 5 moles, preferably about 0.5 to about 1.5 moles, of the latter per mole of the former. The reaction is conducted usually at a temperature in the range of from ambient temperature to about 200° C., preferably about 50 to about 150° C. and is completed usually in several hours to about 25 hours, preferably about 5 to about 15 hours.

The compound of the present invention thus obtained can be readily isolated from the reaction mixture and purified by commonly employed separation and purification means such as recrystallization, column chromatography or the like.

The compound of the present invention can be made into the cyanine compound of the formula (8) by the following process:

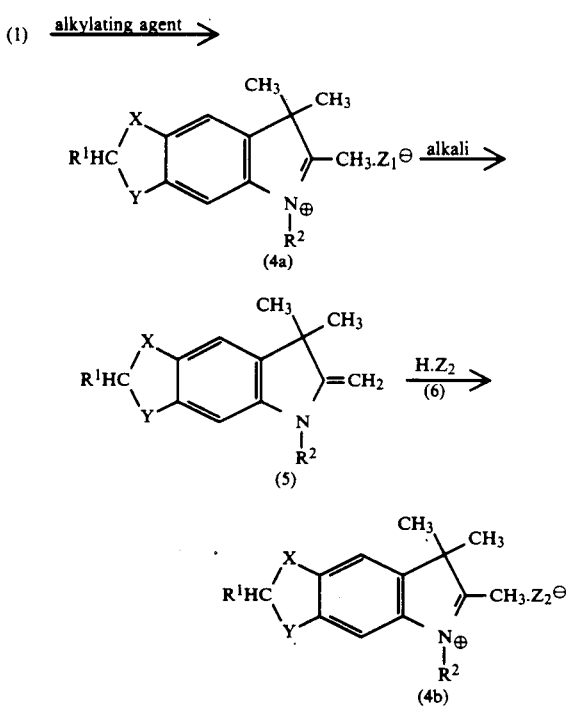

In the above formulas, $R^1$, X and Y are as defined above, $Z_1$ is an acidic residue other than perchlorate residue and tetrafluoroborate residue, $Z_2$ is a perchlorate residue or a tetrafluoroborate residue, and $R^2$ is an optionally substituted lower alkyl group.

The compound represented by the formula (4a) can be prepared by causing an alkylating agent to act on the indolenine derivative of the formula (1). Examples of the alkylating agent are methyl toluenesulfonate, ethyl toluenesulfonate, n-propyl toluenesulfonate, isopropyl toluenesulfonate, n-butyl toluenesulfonate and like alkyl toluenesulfonates, ethyl bromide, n-propyl bromide, n-butyl bromide, ethyl iodide, n-propyl iodide, n-propyl chloride, n-butyl chloride and like halogenated alkyls, dimethyl sulfate, diethyl sulfate and like dialkyl sulfates, a mixture of acids and epoxy compounds (for example, a mixture of hydrochloric acid, sulfuric acid or like inorganic acid, acetic acid, propionic acid or like organic acid and ethylene oxide, propylene oxide or the like), methyl sultone, ethyl sultone, propyl sultone, butyl sultone and like alkyl sultones, etc. The amount of the alkylating agent to be used is usually about 0.3 to about 5 moles, preferably about 0.5 to about 2 moles, per mole of the compound of the formula (1). The reaction is carried out in the presence or the absence of a solvent. Illustrative of useful solvents are toluene, xylene and like alkylbenzenes; n-octane, n-decane, cyclohexane, decalin and like aliphatic hydrocarbons; benzene, napthalin, tetralin and like aromatic hydrocarbons; trichloroethane, tetrachloroethane, chlorobenzene, dichlorobenzene and like halogenated hydrocarbons, etc. The reaction is effected usually at a temperature in the range of from room temperature to about 200° C., preferably about 50° to about 150° C., and is completed in usually about 2 to about 30 hours, preferably about 5 to about 25 hours.

The compound of the formula (5) can be prepared by treating the compound of the formula (4a) with alkali in a suitable solvent such as water. Useful alkalis can be any of those heretofore used, such as sodium hydroxide, potassium hydroxide and the like. The alkali is used in an amount of about 1 to about 20 moles, preferably about 1 to about 5 moles, per mole of the compound of the formula (4a). The amount of the solvent to be used is usually about 2 to about 100 moles, preferably about 2 to about 20 moles, per mole of the compound of the formula (4a). The reaction is performed usually at 0° to about 150° C., preferably 0° to about 100° C., and is completed usually in tens of minutes to about 10 hours, preferably about 1 to about 5 hours.

The compound of the formula (4b) can be produced by reacting the compound of the formula (5) with the compound of the formula (6) in an appropriate solvent such as methanol, ethanol, n-propyl alcohol, isopropyl alcohol, n-butanol, isobutyl alcohol, tert-butyl alcohol and like alcohols; benzene, toluene, xylene, n-octane, n-decane, cyclohexane, decalin, trichloroethane, tetrachloroethane, chlorobenzene, dichlorobenzene and like hydrocarbons, etc. The proportions of the compounds of the formulas (5) and (6) are about 0.3 to about 10 moles, preferably about 0.5 to about 3 moles, of the latter per mole of the former. The reaction is conducted at 0° to about 70° C. and is usually completed in about 10 minutes to about 3 hours.

The cyanine compounds represented by the formula

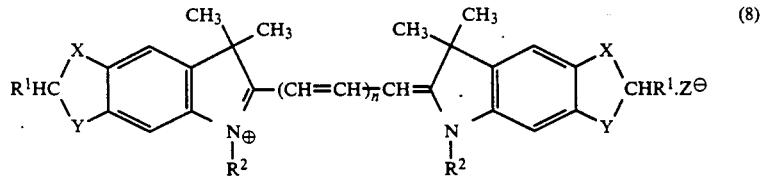

wherein $R^1$, $R^2$, X and Y are as defined above, Z is an acidic residue, and n is 2 or 3, can be prepared by subjecting to condensation reaction the indolenium salt (the compounds of the formulas (4a) and (4b)) obtained above and a known compound represented by the formula

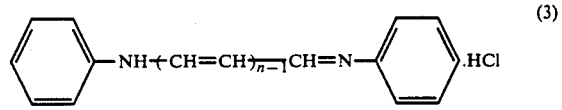

wherein n is as defined above.

Shown below are specific examples of the groups represented by $R^1$, $R^2$ and Z in the formula (8).

Examples of the lower alkyl group are methyl, ethyl, n-propyl, isopropyl, n-butyl, isobutyl, tert-butyl, n-hexyl, n-heptyl, n-octyl and like $C_1$-$C_8$ alkyl groups.

Examples of the substituents for the lower alkyl group are $C_1$-$C_8$ alkoxy, hydroxy, sulfonic acid group, carboxy, ($C_1$-$C_8$ alkyl)amino, phenylsulfonyl amino, p-methylphenylsulfonyl amino, acetoxy, ($C_1$-$C_3$ alkoxy)carbonyl, ($C_1$-$C_3$ alkoxy) ($C_1$-$C_3$ alkoxy)carbonyl and the like. Specific examples of the lower alkyl group having such substituents are methoxymethyl, ethoxymethyl, 2-methoxyethyl, 2-ethoxyethyl, 2-(n-butoxy)ethyl, n-butoxymethyl, 2-hydroxyethyl, a group —$(CH_2)_m$—$SO_3Na$ (wherein m is an integer of 1 to 8), methylaminomethyl, dimethylaminomethyl, 2-(p-methylphenylsulfonylamino)ethyl, acetoxymethyl, methoxycarbonylmethyl, methoxymethoxymethyl, 2-ethoxyethoxyethyl, etc.

Examples of the group Z are halogen atom, alkyl sulfonate residue, arylsulfonate residue, perchlorate residue, tetrafluoroborate residue, arylcarboxylic acid residue and the like. When Z is a halogen atom, examples of $Z^-$ are $Cl^-$, $Br^-$, $I^-$, $F^-$ and the like. When Z is an alkyl sulfate residue, examples of $Z^-$ are $CH_3SO_4^-$, $C_2H_5SO_4^-$, n-$C_3H_7SO_4^-$, n-$C_4H_9SO_4^-$ and the like. When Z is an arylsulfonate residue, examples of $Z^-$ are

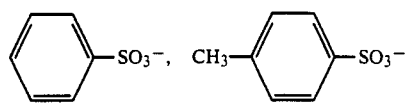

and the like. When Z is a perchlorate residue, examples of $Z^-$ include $ClO_4^-$ and the like. When Z is a tetrafluoroborate residue, examples of $Z^-$ include $BF_4^-$ and the like. When Z is an arylcarboxylic acid residue, examples of $Z^-$ are

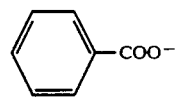

and the like.

The foregoing condensation reaction is conducted in an anhydrous organic solvent in the presence of a fatty acid salt. Useful fatty acid salts are, for example, sodium acetate, potassium acetate, calcium acetate, sodium propionate, potassium propionate and the like. The fatty acid salt is used usually in an amount of about 0.5 to about 3 moles, preferably about 1 to about 2 moles, per mole of the compound of the formula (4a) or (4b). Examples of the anhydrous organic acid are acetic anhydride, propionic anhydride, butyric anhydride, γ-butyrolactone and the like. Such anhydrous organic acid is used usually in an amount of about 10 to about 100 moles, preferably about 20 to about 50 moles, per mole of the compound of the formula (4a) or (4b). The proportions of the compound of the formula (4a) or (4b) and the compound of the formula (7) are about 0.2 to about 1.5 moles, preferably about 0.4 to about 0.7 mole, of the latter per mole of the former. The reaction smoothly proceeds at a temperature of about 50° to about 150° C., preferably about 70° to about 140° C., and is usually completed in about 10 to about 60 minutes.

The compound prepared by any of the foregoing processes can be isolated from the reaction mixture and purified with ease by usual separation and purification means such as recrystallization, column chromatography or the like.

The cyanine compounds of the formula (8) obtained above are useful for the following applications. More specifically, the cyanine compounds of the formula (8) has a good solubility in an organic solvent such as methanol, ethanol, n-propyl alcohol, isopropyl alcohol, n-butanol, isobutanol, tert-butanol, diacetone alcohol or like alcohol, dichloromethane, dichloroethane or like aliphatic halogenated hydrocarbons, or the like. The compounds of the invention have an maximum absorption at 670 to 830 nm and has a high molar absorptivity coefficient. When used as an optical disc recording medium adapted for semiconductor laser recording, the compounds exhibit an outstanding optical reflectivity on exposure to the laser beam for reproduction, hence especially valuable for use. Further, the compounds of the formula (8) which are capable of achieving a marked absorption as compared with usual dyes are suitable for use as a dye for filters, or as a photosensitive material or a sensitizing dye for photosensitive materials in copying and printing. Moreover, the compounds are usable as an agent for medical diagnosis for examining the function of livers, as a dye for Langmuir-Blodgett film, etc.

In addition, the compounds of the invention are useful as intermediates for production of functional dyes such as photochromic materials or the like.

EXAMPLES

Given below are Examples illustrating the preparation of the compounds of the present invention and Reference Examples illustrating the preparation of the compounds of the formula (8).

EXAMPLE 1

A mixture of 20.57 g of 3,4-methylenedioxyaniline, 24.76 g of 3-bromo-3-methyl-2-butanone and 75 ml of pyridine was reacted at a temperature of 50° to 55° C. for 5 hours and further reacted with refluxing for 10 hours. After completion of the reaction, the reaction mixture was added to 100 ml of water and the solution was extracted with 50 ml of dichloromethane. After removal of the solvent, the residue was subjected to vacuum distillation, giving 11.64 g of 2,3,3-trimethyl-5,6-methylenedioxyindolenine.

Boiling point: 134° to 136° C./4 to 5 mmHg.

| Elemental analysis | C | H | N |
|---|---|---|---|
| Found (%) | 70.6 | 6.5 | 6.7 |
| Calcd. (%) | 70.92 | 6.45 | 6.89 |

EXAMPLE 2

A mixture of 20.00 g of 5-aminoindane, 27.23 g of 3-bromo-3-methyl-2-butanone and 60 ml of pyridine was treated in the same manner as in Example 1, giving 17.60 g of the compound of the formula (1) (wherein $R^1$=H, X=methylene, Y=methylene).

Boiling point: 122° to 130° C./3 to 4 mmHg.

| Elemental analysis | C | H | N |
|---|---|---|---|
| Found (%) | 84.3 | 8.7 | 6.9 |
| Calcd. (%) | 84.37 | 8.60 | 7.03 |

EXAMPLE 3

The same procedure as in Example 1 was repeated using 19.76 g of the compound of the formula (2) (wherein $R^1$=methyl, X=O, Y=methylene), giving 11.72 g of the compound of the formula (1) (wherein $R^1$=methyl, X=O, Y=methylene).

Boiling point: 139° to 145° C./5 to 6 mmHg.

| Elemental analysis | C | H | N |
|---|---|---|---|
| Found (%) | 77.9 | 8.1 | 6.4 |
| Calcd. (%) | 78.10 | 7.96 | 6.51 |

EXAMPLE 4

A 11.65 g quantity of the compound of the formula (1) (wherein $R^1$=methyl, X=methylene, Y=O) was prepared in the same manner as in Example 1 using 19.76 g of the compound of the formula (2) (wherein $R^1$=methyl, X=methylene, Y=O).

Boiling point: 130° to 135° C./3 to 4 mmHg.

| Elemental analysis | C | H | N |
|---|---|---|---|
| Found (%) | 77.8 | 8.1 | 6.3 |
| Calcd. (%) | 78.10 | 7.96 | 6.51 |

REFERENCE EXAMPLE 1

A mixture of 10.16 g of 2,3,3-trimethyl-5,6-methylenedioxyindolenine obtained above in Example 1, 13.67 g of n-butyl p-toluenesulfonate and 40 ml of chlorobenzene was reacted with refluxing for 20 hours. After completion of the reaction, 1-(n-butyl)-2,3,3-trimethyl-5,6-methylenedioxyindolenium.toluenesulfonate was extracted with 60 ml of water.

To the extract was added 20 g of 20% NaOH and the mixture was reacted at 70° C. for 3 hours, followed by extraction with 30 ml of toluene. After the toluene was distilled off, the residue was subjected to vacuum distillation, giving 5.25 g of 1-(n-butyl)-3,3-dimethyl-2-methylene-5,6-methylenedioxyindoline.

Boiling point: 162° to 164° C./5 to 6 mmHg.

A 3.24 g quantity of 70% HClO$_4$ was added to a mixture of 5.00 g of 1-(n-butyl)-3,3-dimethyl-2-methylene-5,6-methylenedioxyindoline obtained above and 100 ml of isopropyl alcohol at a temperature of up to 20° C. The mixture obtained was stirred at room temperature for 1 hour and cooled to not higher than 5° C. The precipitated crystals were separated by filtration, washed and dried, giving 6.94 g of 1-(n-butyl)-2,3,3-trimethyl-5,6-methylenedioxyindolenium.perchlorate.

Melting point: 147.0° to 150.0° C.

To 20 ml of acetic anhydride were added 1.45 g of 1-(n-butyl)-2,3,3-trimethyl-5,6-methylenedioxyindolenium.perchlorate, 0.52 g of β-anilino-acrolein-anile hydrochloride and 0.68 g of potassium acetate. The resulting mixture was refluxed for 10 minutes and poured into 100 ml of water. The precipitated crystals were separated by filtration, washed with water and recrystallized from methanol, giving 1.05 g of the compound of the formula (8) (wherein $R^1$=H, $R^2$=n-butyl, X=O, Y=O, $Z^-$=ClO$_4^-$, n=2). Given below are the melting point, wavelength at maximum absorption (λmax) and molar absorptivity coefficient (ε) of the obtained compound.

Melting point: 242.0° to 243.0° C.

λmax: 696 nm (methanol).
ε: $1.76 \times 10^5$ cm$^{-1}$·M$^{-1}$.

REFERENCE EXAMPLE 2

A 5.20 g quantity of the compound of the formula (8) (wherein $R^1$=H, $R^2$=ethyl, X=O, $Z^-$=I$^-$, n=2) was prepared in the same manner as in Reference Example 1 using 10.15 g of the compound of the formula (1) (wherein $R^1$=H, X=O, Y=O).

The wavelength at maximum absorption (λmax) of the obtained compound was 694 nm (methanol).

REFERENCE EXAMPLE 3

The same procedure as in Reference Example 1 was repeated using 15.00 g of the compound of the formula (1) (wherein $R^1$=H, X=O, Y=O), giving 6.00 g of the compound of the formula (8) (wherein $R^1$=H, $R^2$=2-methoxyethyl, X=O, Y=O, $Z^-$=ClO$_4^-$, n=3).

The obtained compound had a wavelength of 793 nm (methanol) at maximum absorption (λmax).

REFERENCE EXAMPLE 4

A 2.09 g quantity of the compound of the formula (8) (wherein $R^1$=methyl, $R^2$=n-butyl, X=O, Y=methylene, $Z^-$=ClO$_4^-$, n=2) was prepared in the same manner as in Reference Example 1 using 6.45 g of the compound of the formula (1) (wherein $R^1$=methyl, X=O, Y=methylene). Given below are the melting point, wavelength at maximum absorption (λmax) and molar absorptivity coefficient (ε) of the thus obtained compound.

Melting point: 227° to 228° C.
λmax: 695 nm (diacetone alcohol).
ε: $1.94 \times 10^5$ cm$^{-1}$.

REFERENCE EXAMPLE 5

The same procedure as in Reference Example 1 was repeated using 6.45 g of the compound of the formula (1) (wherein $R^1$=methyl, X=methylene, Y=O), giving 2.76 g of the compound of the formula (8) (wherein $R^1$=methyl, $R^2$=n-butyl, X=methylene, Y=O, $Z^-$=ClO$_4^-$, n=2). The compound had a melting point, wavelength at maximum absorption (λmax) and molar absorptivity coefficient (ε) as shown below:

Melting point: 215° to 217° C.
λmax: 688 nm (diacetone alcohol).
ε: $1.90 \times 10^5$ cm$^{-1}$.

REFERENCE EXAMPLE 6

A 2.20 g quantity of the compound of the formula (8) (wherein $R^1$=H, $R^2$=n-butyl, X=methylene, Y=methylene, $Z^-$=ClO$_4^-$, n=2) was obtained by conducting the same procedure as in Reference Example 1 using 4.00 g of the compound of the formula (1) (wherein $R^1$=H, X=methylene, Y=methylene). Given below are the melting point, wavelength at maximum absorption (λmax) and molar absorptivity coefficient (ε) of the obtained compound.

Melting point: 163° to 165° C.
λmax: 670 nm (diacetone alcohol).
ε: $2.24 \times 10^5$ cm$^{-1}$.

REFERENCE EXAMPLE 7

The compound of the formula (8) (wherein $R^1$=H, $R^2$=2-ethoxyethyl, X=methylene, Y=methylene, $Z^-$=ClO$_4^-$, n=2) was prepared in the same manner as in Reference Example 1 using the compound of the formula (1) (wherein $R^1$=H, X=methylene, Y=methylene). The compound thus obtained had a wavelength at maximum absorption (λmax) and molar absorptivity coefficient (ε) as shown below.

λmax: 672 nm (diacetone alcohol).
ε: $2.20 \times 10^5$ cm$^{-1}$.

REFERENCE EXAMPLE 8

The same procedure as in Reference Example 1 was repeated using the compound of the formula (1) (wherein $R^1$=H, X=methylene, Y=methylene), giving the compound of the formula (8) (wherein $R^1$=H, $R^2$=2-acetoxyethyl, X=methylene, Y=methylene, $Z^-$=BF$_4^-$, n=3). The wavelength at maximum absorption (λmax) and molar absorptivity coefficient (ε) of the obtained compound were as follows.

λmax: 768 nm.
ε: $2.28 \times 10^5$ cm$^{-1}$.

REFERENCE EXAMPLE 9

The compound of the formula (8) (wherein $R^1$=H, $R^2$=2-methoxyethyl, X=methylene, Y=methylene, $Z^-$=I$^-$, n=3) was obtained in the same manner as in Reference Example 1 using the compound of the formula (1) (wherein $R^1$=H, X=methylene, Y=methylene). Given below are the wavelength at maximum absorption (λmax) and molar absorptivity coefficient (ε) of the obtained compound.

λmax: 768 nm.
ε: $2.30 \times 10^5$ cm$^{-1}$.

REFERENCE EXAMPLE 10

The same procedure as in Reference Example 1 was repeated using the compound of the formula (1) (wherein $R^1$=H, X=O, Y=O), giving the compound of the formula (8) (wherein $R^1$=H, $R^2$=2-hydroxyethyl, X=O, Y=O, $Z^-$=

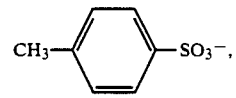

n=2). The obtained compound had a wavelength at maximum absorption (λmax) and molar absorptivity coefficient (ε) as given below.

λmax: 695 nm (diacetone alcohol).
ε: $1.70 \times 10^5$ cm$^{-1}$.

REFERENCE EXAMPLE 11

The compound of the formula (8) (wherein $R^1$=H, $R^2$=—C$_2$H$_4$SO$_3$Na, X=O, Y=O, $Z^-$=Cl$^-$, n=3) was obtained in the same manner as in Reference Example 1 using the compound of the formula (1) (wherein $R^1$=H, X=O, Y=O). Given below are the wavelength at maximum absorption (λmax) and molar absorptivity coefficient (ε) of the obtained compound.

λmax: 790 nm (methanol).
ε: $1.60 \times 10^5$ cm$^{-1}$.

REFERENCE EXAMPLE 12

The same procedure as in Reference Example 1 was repeated using the compound of the formula (1) (wherein $R^1$=methyl, X=O, Y=methylene), giving the compound of the formula (8) (wherein $R^1$=methyl, $R^2$=n-butyl, X=O, Y=methylene, $Z^-$=C$_2$H$_5$SO$_4^-$, n=3). The compound had a wavelength at maximum absorption (λmax) and molar absorptivity coefficient (ε) as shown below.

λmax: 795 nm (methanol).

ε: $1.93 \times 10^5$ cm$^{-1}$.

We claim:

1. An indolenine derivative represented by the formula

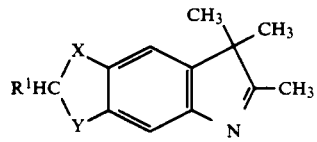

wherein $R^1$ is a hydrogen atom or a lower alkyl group, X and Y are the same or different and each represent a methylene group or an oxygen atom.

2. A compound according to claim 1 wherein X and Y are both a methylene group.

3. A compound according to claim 1 wherein X and Y are both an oxygen atom.

4. A compound according to claim 1 wherein X is a methylene group and Y is an oxygen atom.

5. A compound according to claim 1 wherein X is an oxygen atom and Y is a methylene group.

* * * * *